US006240927B1

(12) United States Patent
Taheri

(10) Patent No.: US 6,240,927 B1
(45) Date of Patent: Jun. 5, 2001

(54) DIAPHRAMATIC MYOPLASTY

(76) Inventor: Syde A. Taheri, 268 Dan-Troy, Williamsville, NY (US) 14221

( * ) Notice: Subject to any disclaimer, the term of this patent is extended or adjusted under 35 U.S.C. 154(b) by 0 days.

(21) Appl. No.: 09/388,135

(22) Filed: Sep. 1, 1999

Related U.S. Application Data
(60) Provisional application No. 60/120,830, filed on Feb. 19, 1999.

(51) Int. Cl.[7] .................................................. A61B 19/00
(52) U.S. Cl. ............................................................... 128/898
(58) Field of Search ............................ 128/898; 600/201, 600/204; 623/8, 66

(56) References Cited
U.S. PATENT DOCUMENTS
5,301,692 * 4/1994 Knowlton ............................. 128/898
5,613,937 * 3/1997 Garrison et al. ..................... 128/898

* cited by examiner

*Primary Examiner*—David J. Isabella

(57) ABSTRACT

A novel surgical procedure directed to improvement of the diaphramatic muscle function is described. This is accomplished by isolation of the latissimus dorsi muscle and relocation to the plural cavity. The latissimus dorsi muscle is then sutured to the diaphragm followed by synchronous stimulation with the patient's respiration.

7 Claims, 1 Drawing Sheet

DIAPHRAMATIC MYOPLASTY

CROSS-REFERENCE TO RELATED APPLICATION

The present application claims priority based on U.S. provisional application Ser. No. 60/120,830, filed Feb. 19, 1999.

BACKGROUND OF THE INVENTION

The present invention relates to a medical procedure for augmenting diaphramatic function. In a healthy person the diaphragm elevates to compress the avioli and distends as the lungs fill with air during an inhalation event. Such diaphramatic function can be hindered for several reasons, including chronic pulmonary obstructive disease, spinal cord injury, diaphramatic muscle dysfunction and paralysis of the diaphragm. For example, chronic pulmonary obstructive disease is a common medical problem associated with an over inflated lung, destruction of the avioli and atrophied diaphramatic muscle. It has been estimated that more than 20 million people suffer from this condition.

Current treatments for chronic pulmonary obstruction disease are based on medical and surgical approaches. Medical approaches generally entail breathing with an inhaler while conventional surgical procedures include lung reduction. These have not improved the outcome and the latter surgical procedures are generally associated with a high incidence of failure. Therefore, the present surgical procedure is an alternate approach which relates to muscle reinforcement of a flattened and weakened diaphragm to provide improved respiration function in patients with impaired diaphramatic function.

SUMMARY OF THE INVENTION

The present invention is a novel surgical procedure directed to improvement of the diaphramatic muscle function. This is accomplished by myoplasty of the diaphramatic muscle and synchronous stimulation with the patient's respiration. The operation is performed as an isolated procedure or in conjunction with a lung reduction operation procedure. After anesthesia and routine preparation, the chest wall muscle is isolated. It is important to preserve the nerve supply for the isolated muscle. The chest wall muscle is brought into the plural cavity and sutured to the diaphragm. Leads from a nerve stimulator are sutured to the nerve supply of the muscle. The transplanted muscle is then stimulated in synchrony with respiration and diaphramatic motion.

The present surgical procedure benefits patients with relatively high pulmonary volume and marked atrophied diaphragm, such as those suffering from chronic obstructive pulmonary disease. These people lack proper diaphramatic function, which conventional medical and surgical approaches have not been entirely successful in restoring.

These and other concepts will become more apparent to those skilled in the art by reference to the following description and the appended drawing.

DETAILED DESCRIPTION OF THE INVENTION

Figure 1:
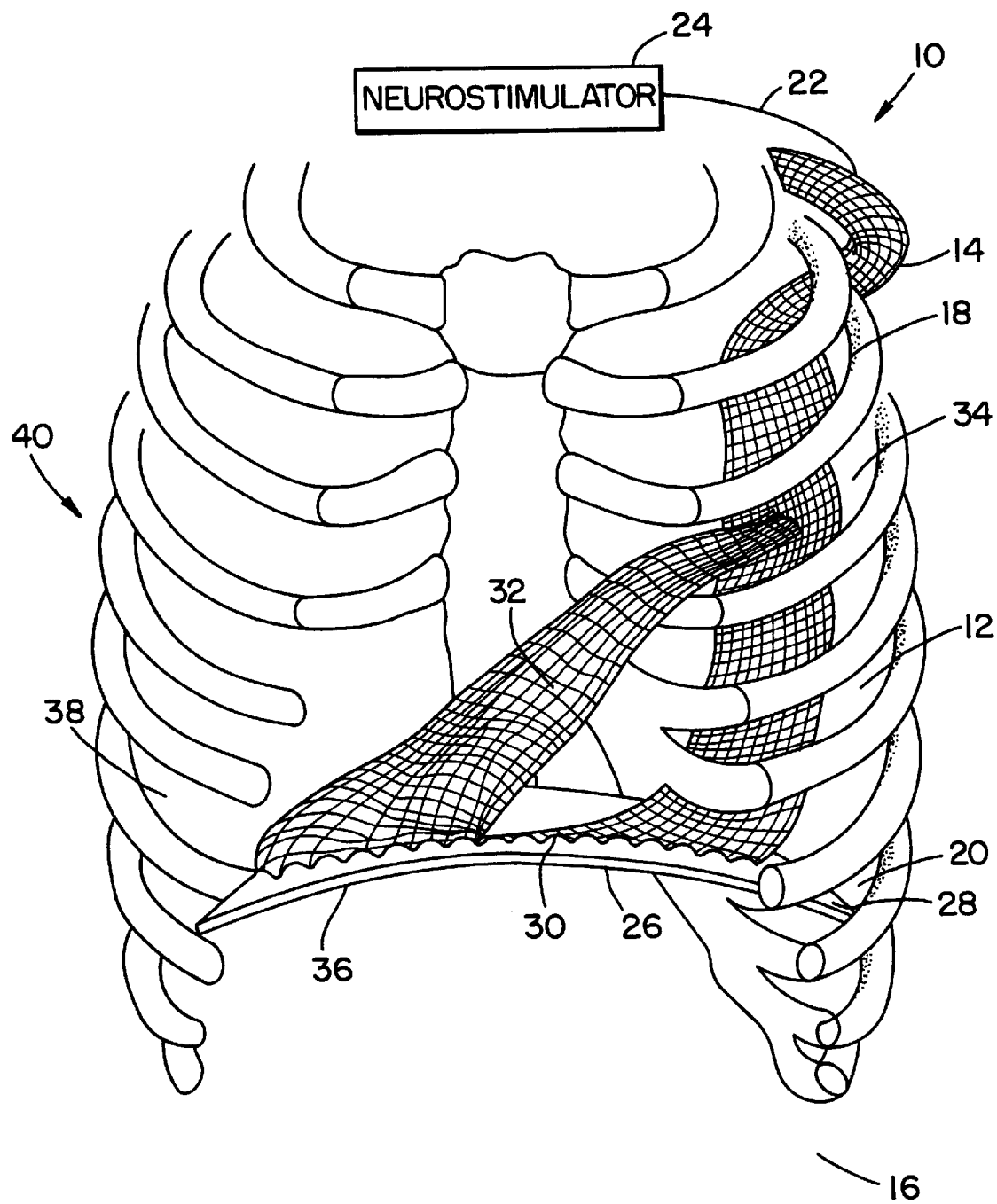
FIG. 1 is a perspective view of the rib cage and a diaphramatic myoplasty procedure according to the present invention.

Turning now to the drawing, a diaphramatic myoplasty procedure according to the present invitation will be described in detail. FIG. 1 shows a skeletal representation of the human rib cage 10 including selected portions of the soft tissue. The present surgical procedure begins with routine surgical preparation. Following general anaesthetic and endotrachial intubation, a limited transauxiliary incision is made over the fifth intercostal space 12. The skin and subcutaneous tissues are incised. With careful sharp and blunt dissection, the right latissimus dorsi muscle 14 is identified and separated from the surrounding muscles. Next, the right latissimus dorsi muscle 14 is divided from its insertion into the iliac crest 16. The right latissimus dorsi muscle 14 is elevated, and the thoraco dorsal nerve and the artery of the latissimus dorsi muscle are then identified and preserved. A thorocotomy is now performed through the second 18 and seventh 20 intercostal space.

Next, the unipolar lead 22 of a neurostimulator 24 is passed perpendicular to the neurovascular bundle, close to the insertion of the right latissimus dorsi muscle to the humeral bone (not shown). A suitable neurostimulator can be purchased from Medtronic, Inc. of Minneapolis, Minn. under the TRANSFORM® label. After satisfactory threshold measurement, the lead 22 is connected to the stimulator and buried under the skin of the chest wall. The right latissimus dorsi muscle 14 is passed through the second intercostal space 18 and retrieved in the seventh intercostal space 20. The right latissimus dorsi muscle 14 is sutured to the dome 26 of the right diaphragm 28 using interrupted sutures 30 followed by continuous sutures. After satisfactory muscle contraction in synchrony with respiration is established by activation of the neurostimulator 24, the thorocotomy and skin incisions are closed.

Contraction of the relocated right latissimus dorsi muscle 14 compresses the overextended avioli (not shown) by upward motion of the diaphragm 28. In that manner, the present diaphramatic myoplasty procedure restores the over distended air space to its normal size.

In FIG. 1, the right latissimus dorsi muscle is shown sutured to the right portion of the diaphragm. The diaphragm is generally divided into a right portion and a left portion, delineated by the heart. This is sufficient for compressing the right lung, but may not necessarily benefit compression of the left avioli. Therefore, the above described procedure is repeated for the left diaphragm. Alternatively, a length of tendon, synthetic muscle 32 or suitable prosthetic material is sutured to the right latissimus dorsi muscle 14 adjacent to the third intercostal space 34 and the left dome 36 of the diaphragm 28 proximate the sixth intercoastal space 38 of the left portion 40 of the rib cage 10. That way, as the right latissimus dorsi muscle 14 contracts, the synthetic muscle 32 is elevated to compress the left avioli. Relaxation of the right latissimus dorsi muscle 14 results in the synthetic muscle 32 decreasing in elevation to allow for an inhalation event.

Other muscles of the human body that are useful for augmenting diaphramatic function according to the present invention include the pectoralis major and the rectus adominus. Adaptation of the present procedure to use of these alternate muscles will be readily understood by those skilled in the art.

The present diaphramatic myoplasty procedure is a novel concept which allows a fibrillated, weak diaphragm muscle to move upward and empty over distended avioli. This novel approach is not only beneficial for thousands of chronic obstructive pulmonary disease cases, but also for patients with spinal cord injury and diaphramatic muscle dysfunction.

It is appreciated that various modifications to the invention concepts described herein may be apparent to those skilled in the art without departing from the spirit and scope of the present invention defined by the hereinafter appended claims.

What is claimed is:

1. A method for restoring impaired diaphramatic muscle function, comprising the steps of:
   (a) identifying and separating a latissimus dorsi muscle from the surrounding muscle;
   (b) dividing the latissimus dorsi muscle from its insertion into the iliac crest;
   (c) identifying and preserving the elevated and thoracal dorsi nerve and artery;
   (d) performing a thorocotomy through the second and seventh intercostal space;
   (e) connecting a neurostimulator to the neurovascular bundle of the latissimus dorsi muscle;
   (f) moving the latissimus dorsi muscle through the second intercostal space and retrieving the latissimus dorsi muscle in the seventh intercostal space; and
   (g) suturing the latissimus dorsi muscle to a dome portion of the diaphragm.

2. The method of claim 1 wherein the latissimus dorsi muscle is isolated from the right rib cage.

3. The method of claim 1 wherein the latissimus dorsi muscle is isolated from the left rib cage.

4. The method of claim 1 wherein the latissimus dorsi muscle is sutured to the right portion of the diaphragm.

5. The method of claim 4 further including connecting a synthetic muscle to the latissimus dorsi muscle and the diaphragm.

6. The method of claim 5 wherein the synthetic muscle is connected to the latissimus dorsi muscle adjacent to the third intercostal space and a left dome portion of the diaphragm proximate the sixth intercostal space.

7. The method of claim 1 wherein the neurostimulator is connected to the neurovascular bundle of the latissimus dorsi muscle proximate the humeral bone.

* * * * *